(12) United States Patent
Fung et al.

(10) Patent No.: US 8,206,934 B2
(45) Date of Patent: Jun. 26, 2012

(54) METHODS FOR DIAGNOSING OVARIAN CANCER

(75) Inventors: Eric Thomas Fung, Los Altos, CA (US); Tai-Tung Yip, Cupertino, CA (US); Vladimir Podust, Castco, CA (US); Mats Brannstrom, Gothenburg (SE); Karin Sundfeldt, Gothenburg (SE); Bjorg Kristjansdottir, Gothenburg (SE)

(73) Assignee: Vermillion, Inc., Austin, TX (US)

( * ) Notice: Subject to any disclaimer, the term of this patent is extended or adjusted under 35 U.S.C. 154(b) by 0 days.

(21) Appl. No.: 12/584,832

(22) Filed: Sep. 11, 2009

(65) Prior Publication Data

US 2010/0047847 A1    Feb. 25, 2010

Related U.S. Application Data

(63) Continuation of application No. 12/079,588, filed on Mar. 27, 2008, now abandoned.

(60) Provisional application No. 60/908,670, filed on Mar. 28, 2007.

(51) Int. Cl.
*G01N 33/53* (2006.01)

(52) U.S. Cl. .......................................... 435/7.1

(58) Field of Classification Search .................. None
See application file for complete search history.

(56) References Cited

U.S. PATENT DOCUMENTS

2006/0029956 A1 *  2/2006  Beyer et al. ...................... 435/6

FOREIGN PATENT DOCUMENTS

| WO | WO-2007/002527 | | 1/2007 |
| WO | WO 2007/035766 | A2 * | 3/2007 |
| WO | WO 2008/048508 | A2 * | 4/2008 |

OTHER PUBLICATIONS

Sieben et al (Journal of Clinical Oncology, Oct. 2005, 23(29):7257-7264).*
Tockman et al (Cancer Res., 1992, 52:2711s-2718s).*
Hazelton et al (Clinical Cancer Research, 1999, 5(4):823-829).*
Zhang et al (Cancer Research, 2004, 64:5882-5890).*
Yoneda et al. Expression of Angiogenesis-Related Genes and Progression of Human Ovarian Carcinomas in Nude Mice. (Journal of National Cancer Institute, Mar. 1998, vol. 90, No. 6, pp. 447-460).

* cited by examiner

*Primary Examiner* — Sean Aeder
(74) *Attorney, Agent, or Firm* — Edwards Wildman Palmer LLP; Peter F. Corless; Andrew W. Shyjan

(57) ABSTRACT

The present invention provides protein-based biomarkers and biomarker combinations that are useful in qualifying ovarian cancer status in a patient. In particular, the biomarkers of this invention are useful to classify a subject sample as ovarian cancer, ovarian cancer of low malignant potential, benign ovarian disease or other malignant condition. The biomarkers can be detected by SELDI mass spectrometry, immunoassay, or other means.

2 Claims, 2 Drawing Sheets

SEQUENCE LISTING

<160> NUMBER OF SEQ ID NOS: 9

<210> SEQ ID NO 1
<211> LENGTH: 30
<212> TYPE: PRT
<213> ORGANISM: Homo sapiens

<400> SEQUENCE: 1

Met Asn Phe Arg Pro Gly Val Leu Ser Ser Arg Gln Leu Gly Leu Pro
1               5                   10                  15

Gly Pro Pro Asp Val Pro Asp His Ala Ala Tyr His Pro Phe
            20                  25                  30

<210> SEQ ID NO 2
<211> LENGTH: 25
<212> TYPE: PRT
<213> ORGANISM: Homo sapiens

<400> SEQUENCE: 2

Asp Thr His Phe Pro Ile Cys Ile Phe Cys Cys Gly Cys Cys His Arg
1               5                   10                  15

Ser Lys Cys Gly Met Cys Cys Lys Thr
            20                  25

<210> SEQ ID NO 3
<211> LENGTH: 24
<212> TYPE: PRT
<213> ORGANISM: Homo sapiens

<400> SEQUENCE: 3

Thr His Phe Pro Ile Cys Ile Phe Cys Cys Gly Cys Cys His Arg Ser
1               5                   10                  15

Lys Cys Gly Met Cys Cys Lys Thr
            20

<210> SEQ ID NO 4
<211> LENGTH: 20
<212> TYPE: PRT
<213> ORGANISM: Homo sapiens

<400> SEQUENCE: 4

Ile Cys Ile Phe Cys Cys Gly Cys Cys His Arg Ser Lys Cys Gly Met
1               5                   10                  15

Cys Cys Lys Thr
            20

<210> SEQ ID NO 5
<211> LENGTH: 22
<212> TYPE: PRT
<213> ORGANISM: Homo sapiens

<400> SEQUENCE: 5

Phe Pro Ile Cys Ile Phe Cys Cys Gly Cys Cys His Arg Ser Lys Cys
1               5                   10                  15

Gly Met Cys Cys Lys Thr
            20

<210> SEQ ID NO 6
<211> LENGTH: 76
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Pyrrolidone carboxylic acid

<400> SEQUENCE: 6

Xaa Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
            35                  40                  45

Lys Glu Ile Cys Ala Asp Pro Lys Gln Lys Trp Val Gln Asp Ser Met
50                      55                  60

Asp His Leu Asp Lys Gln Thr Gln Thr Pro Lys Thr
65                  70                  75

<210> SEQ ID NO 7
<211> LENGTH: 77
<212> TYPE: PRT
<213> ORGANISM: Homo sapiens

<400> SEQUENCE: 7

Ala Val Leu Pro Arg Ser Ala Lys Glu Leu Arg Cys Gln Cys Ile Lys
1               5                   10                  15

Thr Tyr Ser Lys Pro Phe His Pro Lys Phe Ile Lys Glu Leu Arg Val
            20                  25                  30

Ile Glu Ser Gly Pro His Cys Ala Asn Thr Glu Ile Ile Val Lys Leu
            35                  40                  45

Ser Asp Gly Arg Glu Leu Cys Leu Asp Pro Lys Glu Asn Trp Val Gln
50                  55                  60

Arg Val Val Glu Lys Phe Leu Lys Arg Ala Glu Asn Ser
65                  70                  75

<210> SEQ ID NO 8
<211> LENGTH: 72
<212> TYPE: PRT
<213> ORGANISM: Homo sapiens

<400> SEQUENCE: 8

Ser Ala Lys Glu Leu Arg Cys Gln Cys Ile Lys Thr Tyr Ser Lys Pro
1               5                   10                  15

Phe His Pro Lys Phe Ile Lys Glu Leu Arg Val Ile Glu Ser Gly Pro
            20                  25                  30

His Cys Ala Asn Thr Glu Ile Ile Val Lys Leu Ser Asp Gly Arg Glu
            35                  40                  45

Leu Cys Leu Asp Pro Lys Glu Asn Trp Val Gln Arg Val Val Glu Lys
50                  55                  60

Phe Leu Lys Arg Ala Glu Asn Ser
65                  70

<210> SEQ ID NO 9
<211> LENGTH: 5
<212> TYPE: PRT
<213> ORGANISM: Homo sapiens

<400> SEQUENCE: 9

Ala Val Leu Pro Arg
1               5

METHODS FOR DIAGNOSING OVARIAN CANCER

This application claims the benefit of U.S. application Ser. No. 12/079,588, filed Mar. 27, 2008 and U.S. Provisional Application No. 60/908,670, filed Mar. 28, 2007, the entire contents of which are hereby incorporated herein by reference.

SEQUENCE LISTING

The instant application contains a Sequence Listing which has been submitted via EFS-Web and is hereby incorporated by reference in its entirety. Said ASCII copy, created on Jul. 26, 2010, is named 68840CON.txt and is 4,061 bytes in size.

FIELD OF THE INVENTION

This invention relates generally to clinical diagnostics and, in particular, to clinical diagnostics for ovarian cancer.

BACKGROUND OF THE INVENTION

Ovarian cancer is among the most lethal gynecologic malignancies in developed countries. Annually, in the United States alone, approximately 23,000 women are diagnosed with the disease and almost 14,000 women die from it. (Jamal et al., *CA Cancer J. Clin.*, 52:23-47 (2002)). Despite progress in cancer therapy, ovarian cancer mortality has remained virtually unchanged over the past two decades. (Id.) Given the steep survival gradient relative to the stage at which the disease is diagnosed, early detection remains the most important factor in improving long-term survival of ovarian cancer patients.

The poor prognosis of ovarian cancer diagnosed at late stages, the cost and risk associated with confirmatory diagnostic procedures, and its relatively low prevalence in the general population together pose extremely stringent requirements on the sensitivity and specificity of a test for it to be used for screening for ovarian cancer in the general population The identification of tumor markers suitable for the early detection and diagnosis of cancer holds great promise to improve the clinical outcome of patients. It is especially important for patients presenting with vague or no symptoms or with tumors that are relatively inaccessible to physical examination. Despite considerable effort directed at early detection, no cost effective screening tests have been developed (Paley, *Curr. Opin. Oncol.*, 13(5):399402 (2001)) and women generally present with disseminated disease at diagnosis. (Ozols et al., Epithelial ovarian cancer. In: Hoskins W J, Perez C A, Young R C, editors. Principles and Practice of Gynecologic Oncology. 3rd ed. Philadelphia: Lippincott, Williams and Wilkins; pages 981-1057 (2000)).

The best-characterized tumor marker, CA125, is negative in approximately 30-40% of stage I ovarian carcinomas and its levels are elevated in a variety of benign diseases. (Meyer et al., *Br. J. Cancer*, 82(9):1535-8 (2000); Buamah, *J. Surg. Oncol.*, 75(4):264-5 (2000); Tuxen et al., *Cancer Treat. Rev.*, 21(3):215-45 (1995)). Its use as a population-based screening tool for early detection and diagnosis of ovarian cancer is hindered by its low sensitivity and specificity (MacDonald et al., *Eur. J. Obstet. Gynecol. Reprod. Biol.*, 82(2):155-7 (1999); Jacobs et al., *Hum. Reprod.*, 4(1):1-12 (1989); Shih et al., Tumor markers in ovarian cancer, Diamandis, Fritsche, Lilja, Chan, and Schwartz, editor; Tumor markers physiology, pathobiology, technology and clinical applications, Philadelphia: AACC Press; in press). Although pelvic and more recently vaginal sonography has been used to screen high-risk patients, neither technique has the sufficient sensitivity and specificity to be applied to the general population (MacDonald et al., supra). Recent efforts in using CA125 in combination with additional tumor markers (Woolas et al., *J. National Cancer Inst.*, 85(21):1748-51 (1993); Woolas et al., *Gynecol. Oncol.*, 59(1):111-6 (1995); Zhang et al., *Gynecol. Oncol.*, 73(1):56-61 (1999); Zhang et al., Use of Multiple Markers to Detect Stage I Epithelial Ovarian Cancers: Neural Network Analysis Improves Performance, American Society of Clinical Oncology (2001); Annual Meeting, Abstract) in a longitudinal risk of cancer model (Skates et al., *Cancer*, 76(10 Supp): 2004-10 (1995)), and in tandem with ultrasound as a second line test (Jacobs et al., *Br. Med. J.*, 306(6884):1030-34 (1993); Menon et al., *British Journal of Obstetrics and Gynecology*, 107(2):165-69 (2000)) have shown promising results in improving overall test specificity, which is critical for a disease such as ovarian cancer that has a relatively low prevalence.

Due to the dismal prognosis of late stage ovarian cancer, it is the general consensus that a physician will accept a test with a minimal positive predictive value of 10%. (Bast et al., *Cancer Treatment and Research*, 107:61-97 (2002)). Extending this to the general population, a general screening test would require a sensitivity greater than 70% and a specificity of 99.6%. Currently, none of the existing serologic markers, such as CA125, CA72-4, or M-CSF, individually delivers such a performance (Bast et al., *Int. J. Biol. Markers*, 13:179-87 (1998)).

Thus, there is a critical need for new serological markers that individually or in combination with other markers or diagnostic modalities deliver the required sensitivity and specificity for early detection of ovarian cancer (Bast et al., Early detection of ovarian cancer: promise and reality, In: Stack M S, Fishman D A, editors; Ovarian cancer. Boston, Mass.: Kluwer Publishers (2002) p. 61-97 (Cancer Treat Res (2002); 107:61-97)). Without an acceptable screening test, early detection remains the most critical factor in improving long-term survival of patients with ovarian cancer.

Thus, it is desirable to have a reliable and accurate method of determining the ovarian cancer status in patients, the results of which can then be used to manage subject treatment.

SUMMARY OF THE INVENTION

The present invention fills these needs by providing novel biomarkers and combinations of biomarkers useful for diagnosing ovarian cancer, as well as methods and kits for using the biomarkers to diagnose ovarian cancer.

More specifically, in one aspect, the present invention provides a method for qualifying ovarian cancer status in a subject comprising: (a) measuring at least one biomarker in a biological sample from the subject, wherein the at least one biomarker is selected from the group consisting of the biomarkers of Table 1; and (b) correlating the measurement with ovarian cancer status.

In another embodiment, the method further comprises measuring some other known biomarker for ovarian cancer, such as CA125. In a further embodiment, the method further comprises measuring and correlating at least one biomarker selected from the group consisting of CA125, transferrin, haptoglobin, ApoA1, transthyretin, ITIH4 internal fragment, beta 2-microglobulin, hepcidin, prostatin, osteopontin, esoinophil-derived neurotoxin, leptin, prolactin, IGF-II, hemoglobin and modified forms thereof. In yet another embodiment, the method further comprises measuring CA125 II, CA15-3, CA19-9, CA72-4, CA 195, tumor associated trypsin inhibitor (TATI), CEA, placental alkaline phosphatase (PLAP), Sialyl TN, galactosyltransferase, macrophage colony stimulating factor (M-CSF, CSF-1), lysophosphatidic acid (LPA), 110 kD component of the subject, extracellular domain of the epidermal growth factor receptor (p110EGFR), tissue kallikreins, e.g., kallikrein 6 and kallikrein 10 (NES-1), prostasin, HE4, creatine kinase B (CKB), LASA, HER-2/neu, urinary gonadotropin peptide, Dianon NB 70/K, Tissue peptide antigen (TPA), SMRP, osteopontin, and haptoglobin, leptin, prolactin, insulin-like growth factor I and insulin-like growth factor II. These additional biomarkers can also be measured and correlated using the other methods, kits and software of the present invention.

In one embodiment of the above method, the at least one biomarker is measured by capturing the biomarker on an adsorbent surface of a SELDI probe and detecting the captured biomarkers by laser desorption-ionization mass spectrometry. In another embodiment, the at least one biomarker is measured by an immunoassay. This latter method is particularly useful when the identity of the biomarker is known. In one embodiment, the sample is ovarian cyst fluid. In a related embodiment, the adsorbent is a member selected from the group consisting of a hydrophobic adsorbent, an anion exchange adsorbent, a cation exchange adsorbent and a metal chelate adsorbent. In yet another embodiment, the adsorbent is a cation exchange adsorbent.

In another embodiment, the biomarkers of the invention are measured by a method other than mass spectrometry or methods that rely on a measurement of the mass of the biomarker. For instance, in certain embodiments, the biomarkers of this invention are measured by immunoassay.

As indicated, the above method is directed to qualifying ovarian cancer status. In one embodiment, the correlating is performed by a software classification algorithm. Generally, in the method of the present invention, the ovarian cancer status is selected from benign ovarian disease, ovarian cancer of low malignant potential, ovarian cancer (malignant) and other malignant conditions. In one embodiment, the ovarian cancer status is selected from benign ovarian disease and ovarian cancer of low malignant potential versus ovarian cancer (malignant) and other malignant conditions. In another embodiment, the ovarian cancer status is selected from ovarian cancer of low malignant potential versus benign ovarian disease, ovarian cancer (malignant) and other malignant conditions. In yet another embodiment, the ovarian cancer status rules out the possibility of benign ovarian disease. In still a further embodiment, the ovarian cancer status rules out the possibility of ovarian cancer (malignant) and other malignant conditions.

In another embodiment, the methods described herein of detecting biomarkers and correlating the measurements with ovarian cancer status further comprise managing subject treatment based on the status. In a related embodiment, if the measurement correlates with ovarian cancer, then managing subject treatment comprises administering a chemotherapeutic agent to the subject. In another embodiment, the methods further comprise measuring the at least one biomarker after subject management and correlating the measurement with disease progression, include determining the rates of disease progression.

The invention also provides a method comprising measuring at least one biomarker in a sample from a subject, wherein the at least one biomarker is selected from the group consisting of biomarkers of Table 1.

Another embodiment of the invention provides a method for determining the course of ovarian cancer comprising (a) measuring, at a first time, at least one biomarker in a biological sample from the subject, wherein the at least one biomarker is selected from the group consisting of the biomarkers of Table 1; and (b) measuring, at a second time, the at least one biomarker in a biological sample from the subject; and (c) comparing the first measurement and the second measurement; wherein the comparative measurements determine the course of the ovarian cancer.

In addition to the methods described herein, the invention also provides compositions comprising a purified biomolecule selected from the biomarkers of Table 1. In another embodiment, the invention provides a composition comprising a biospecific capture reagent, e.g., an antibody, that specifically binds a biomolecule selected from the biomarkers of Table 1. In a related embodiment, the biospecific capture reagent is bound to a solid support. In yet another embodiment, the invention provides a composition comprising a biospecific capture reagent bound to a biomarker of Table 1.

In other embodiments, the invention provides kits. For example, in one embodiment, the invention provides a kit comprising: (a) a solid support comprising at least one capture reagent attached thereto, wherein the capture reagent binds at least one biomarker from a first group consisting of the biomarkers of Table 1; and (b) instructions for using the solid support to detect a biomarker of Table 1. In yet another embodiment, the kits further comprise instructions for using the solid support to detect CA125.

In another related embodiment, the solid support of the kits comprises a capture reagent is a SELDI probe, where the capture reagent is a hydrophobic adsorbent, an anion exchange adsorbent, a cation exchange adsorbent and a metal chelate adsorbent. In yet another embodiment, the kits additionally comprise a container containing at least one of the biomarkers of Table 1. In yet another embodiment, the kits additionally comprise a cation exchange chromatography sorbent.

In another embodiment, the invention provides a kit comprising (a) a solid support comprising at least one capture reagent attached thereto, wherein the capture reagents bind at least one biomarker selected from the group consisting of the biomarkers of Table 1; and (b) a container containing at least one of the biomarkers. In another embodiment, the container further contains CA125.

In yet another embodiment, the solid support of the kits comprises a capture reagent is a SELDI probe, where the capture reagent is a hydrophobic adsorbent, an anion exchange adsorbent, a cation exchange adsorbent and a metal chelate adsorbent. In yet another embodiment, the kits additionally comprise a container containing at least one of the biomarkers of Table 1.

The invention additionally provides a software product comprising code that accesses data attributed to a sample, the data comprising measurement of at least one biomarker in the sample, the biomarker selected from the group consisting of the biomarkers of Table 1; and further comprising code that executes a classification algorithm that classifies the ovarian cancer status of the sample as a function of the measurement. In yet another embodiment, the classification algorithm classifies the ovarian cancer status of the sample further as a function of the measurement of CA125.

The present invention additionally provides a method which comprises detecting a biomarker of Table 1 by mass spectrometry or immunoassay.

In another embodiment, the invention provides a method comprising communicating to a subject a diagnosis relating to ovarian cancer status determined from the correlation of biomarkers in a sample from the subject, wherein the biomarkers are selected from the group consisting of the biomarkers of Table 1. In a related embodiment, the diagnosis is communicated to the subject via a computer-generated medium.

In another embodiment, the present invention provides a method for identifying a compound that interacts with a biomarker of Table 1, wherein the method comprises (a) contacting a biomarker of Table 1 with a test compound; and (b) determining whether the test compound interacts with the biomarker of Table 1.

In another embodiment, the invention provides a method for modulating the concentration of Calgranulin C in a cell, wherein the method comprises contacting said cell with an inhibitor, wherein said inhibitor prevents cleavage of Calgranulin C.

The invention additionally provides a method of treating a condition in a subject, wherein said method comprises administering to a subject a therapeutically effective amount of an inhibitor of Calgranulin C, wherein the inhibitor prevents cleavage of Calgranulin C. In a related embodiment, said condition is ovarian cancer.

The invention also provides a method for determining whether ovarian tissue is cancerous, comprising contacting said ovarian tissue with a detectable agent which specifically associates with a biomarker of Table 1, measuring the level of binding of said agent to said tissue; and correlating said level of binding with the presence or progression of cancer of said tissue.

In another embodiment, the invention provides a method for qualifying ovarian cancer status in a subject comprising measuring at least one biomarker in a biological sample from the subject, wherein the at least one biomarker is selected from the group consisting of IL-8, IL-8 (6-77) and MCP1; and correlating the measurement with ovarian cancer status. In a related embodiment, antibodies are used to purify the biomarkers from ovarian cyst fluid prior to their measurement. In another embodiment, multiple biomarkers are purified and detected using the Antibody Mix I or Antibody Mix II compositions described herein.

Other features, objects and advantages of the present invention and its preferred embodiments will become apparent from the detailed description, examples and claims that follow.

DETAILED DESCRIPTION OF THE INVENTION AND PREFERRED EMBODIMENTS

I. Introduction

Figure 1:
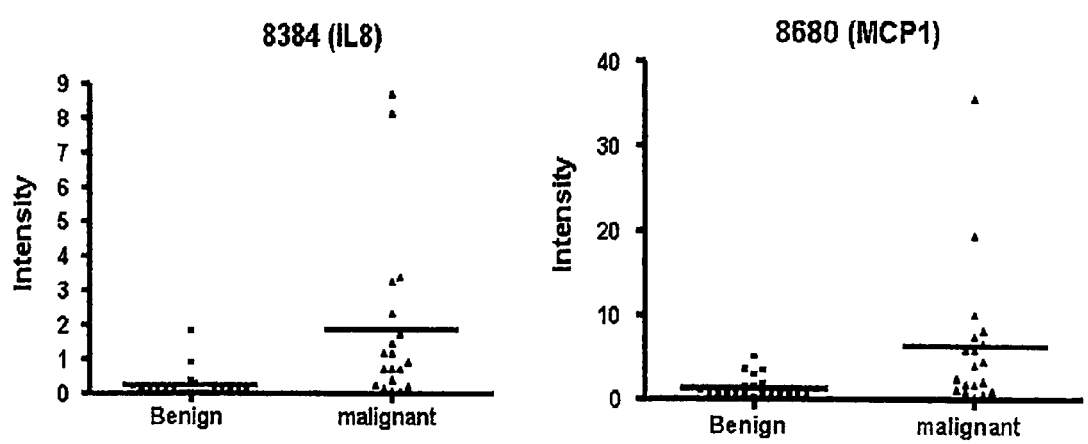
FIG. 1 shows results from the Immunoprecipitation Method obtained for the IL-8 and MCP1 proteins whose expression is increased in patients with malignant ovarian cancer.

A biomarker is an organic biomolecule which is differentially present in a sample taken from a subject of one phenotypic status (e.g., having a disease) as compared with another phenotypic status (e.g., not having the disease). A biomarker is differentially present between different phenotypic statuses if the mean or median expression level of the biomarker in the different groups is calculated to be statistically significant. Common tests for statistical significance include, among others, t-test, ANOVA, Kruskal-Wallis, Wilcoxon, Mann-Whitney and odds ratio. Biomarkers, alone or in combination, provide measures of relative risk that a subject belongs to one phenotypic status or another. Therefore, they are useful as markers for disease (diagnostics), therapeutic effectiveness of a drug (theranostics) and drug toxicity.

II. Biomarkers for Ovarian Cancer

This invention provides polypeptide-based biomarkers that are differentially present in subjects having ovarian cancer, in particular, ovarian cancer (malignant, such as invasive epithelial ovarian cancer), ovarian cancer of low malignant potential ((LMP), borderline disease), benign ovarian disease and other malignant conditions (such as malignancies other than invasive epithelial ovarian cancer, including metastatic cancer (e.g., gastric cancer metastasized to the ovary), mesothelioma, a stromal ovarian cancer, etc.)). The biomarkers are characterized by mass-to-charge ratio as determined by mass spectrometry, by the shape of their spectral peak in time-of-flight mass spectrometry and by their binding characteristics to adsorbent surfaces. These characteristics provide one method to determine whether a particular detected biomolecule is a biomarker of this invention. These characteristics represent inherent characteristics of the biomolecules and not process limitations in the manner in which the biomolecules are discriminated. In one aspect, this invention provides these biomarkers in isolated form.

The biomarkers were discovered using SELDI technology employing ProteinChip arrays from Ciphergen Biosystems, Inc. (Fremont, Calif.) ("Ciphergen"). Ovarian cyst fluid was collected from subjects diagnosed with ovarian cancer (invasive epithelial ovarian cancer), ovarian cancer of low malignant potential (borderline disease), other malignant conditions and benign ovarian disease. A portion of the samples were left unfactionated and the other portion of samples were fractionated by anion exchange chromatography. Unfractionated and fractionated samples were applied to SELDI biochips and spectra of polypeptides in the samples were generated by time-of-flight mass spectrometry on a Ciphergen PBSII mass spectrometer. The spectra thus obtained were analyzed by Ciphergen Express™ Data Manager Software with Biomarker Wizard and Biomarker Pattern Software from Ciphergen Biosystems, Inc. The mass spectra for each group were subjected to scatter plot analysis. A Mann-Whitney test analysis was employed to compare ovarian cancer and control groups for each protein cluster in the scatter plot, and proteins were selected that differed significantly ($p<0.0001$) between the two groups. This method is described in more detail in the Example Section.

The biomarkers thus discovered are presented in Table 1. The "Assay" column refers to a fraction or flowthrough (if applicable) in which the biomarker is found during the course of preparing the ovarian cyst fluid. "AUC" stands for "area under the curve" in a receiver operated curve analysis and corresponds to whether the biomarker is up- or down-regulated in ovarian cancer. An AUC less than 0.5 indicates that the marker is lower in cancerous patients relative to patients with benign tumors. An AUC value greater than 0.5 indicates that the marker is up-regulated in patients with malignant tumors relative to patients with benign ovarian cancer.

TABLE 1

Ovarian Cancer Biomarkers

| P-value | AUC | m/z | Assay* | Identity | Calculated MW |
|---|---|---|---|---|---|
| 3.86E−08 | 0.240043 | M3634.96 | EB-E2 fa | Albumin, N-terminal fragment (SwissProt # P02768), amino acids 27-57 of the precursor sequence | |
| 4.35E−12 | 0.185646 | M3902.281 | EB-E3 fa | Protein C inhibitor, C-terminal fragment (SwissProt# 05154), amino acids 374-406 of the precursor | 3890.61 |
| 2.05E−09 | 0.76684 | M4448.712 | EB-E1 | Alpha-1-antitrypsin, N-terminal fragment (SwissProt# P01009), amino acids 25-63 of the precursor | 4443.73 |
| 6.96E−09 | 0.240043 | M4808.772 | EB-E2 fa | Alpha-1-antitrypsin, C-terminal fragment (SwissProt# P01009), amino acids 377-418 of the precursor | 4789.77 |
| 2.51E−08 | 0.244988 | M4892.11 | MEP-M2 hi | 5023 —Asp | |
| 8.57E−09 | 0.240043 | M5023.014 | MEP-M1 hi | | |
| 1.68E−10 | 0.791566 | M6448.168 | MEP-M1 | ApoCI, 2 amino acids truncation from N-terminus, SwissProt# P02654, amino acids 29-83 of the precursor | 6432.36 |
| 2.09E−09 | 0.769447 | M6645.581 | MEP-M1 hi | ApoCI, full-length protein, SwissProt# P02654, amino acids 27-83 of the precursor | 6630.59 |
| 1.43E−08 | 0.754611 | M8037.936 | FT | Hb beta 2+ | |
| 2.83E−09 | 0.759556 | M9448.429 | EB-E3 | ApoCIII, full-length protein, two glycosylated forms, SwissProt# P02656, amino acids 21-99 of the precursor** | 9421.28 |
| 6.86E−13 | 0.804063 | M9743.119 | EB-E3 fa | ApoCIII, full-length protein, two glycosylated forms, SwissProt# P02656, amino acids 21-99 of the precursor** | 9712.53 |
| 3.80E−08 | 0.764234 | M12863.56 | MEP-M1 hi | SAA4, full-length protein, SwissProt# P35542, amino acids 19-130 of the precursor | 12863.28 |
| 3.73E−10 | 0.769447 | M13900.61 | EB-E3 fa | Transthyretin | |

*EB E2 fa = Equalizer bead eluted fraction 2; fa is short for formic acid, i.e., the array is read by the mass spectrometer after addition of formic acid to the spot with higher laser energy EB E3 fa = Equalizer bead eluted fraction 3; after addition of formic acid to the matrix EB E1 = Equalizer bead eluted fraction 1; first read with lower laser energy MEP M1 hi = MEP bead eluted fraction 1; second read with higher laser energy MEP M2 hi = MEP bead eluted fraction 2; second read with higher laser energy FT = flow through from the beads
**ApoCIII is glycosylated and is present with different oligosaccharide modifications.

The biomarkers of this invention are characterized by their mass-to-charge ratio as determined by mass spectrometry. The mass-to-charge ("m/z") ratio of each biomarker is provided in Table 1, after the "M." Thus, for example, M3634.96 (an N-terminal truncation of albumin) has a measured mass-to-charge ratio of 3634.96. The mass-to-charge ratios were determined from mass spectra generated on a Ciphergen Biosystems, Inc. PBS II mass spectrometer. This instrument has a mass accuracy of about +/−0.15 percent. Additionally, the instrument has a mass resolution of about 400 to 1000 m/dm, where m is mass and dm is the mass spectral peak width at 0.5 peak height. The mass-to-charge ratio of the biomarkers was determined using Biomarker Wizard™ software (Ciphergen Biosystems, Inc.). Biomarker Wizard assigns a mass-to-charge ratio to a biomarker by clustering the mass-to-charge ratios of the same peaks from all the spectra analyzed, as determined by the PBSII, taking the maximum and minimum mass-to-charge ratio in the cluster, and dividing by two. Accordingly, the masses provided reflect these specifications.

The biomarkers of this invention are further characterized by the shape of their spectral peak in time-of-flight mass spectrometry.

The biomarkers of this invention are further characterized by their binding properties on chromatographic surfaces. Examples of chromatographic surfaces that the biomarkers of this invention bind include, but are not limited to, a hydrophobic adsorbent (such as the Ciphergen® H50 ProteinChip® array), an anion exchange adsorbent (such as the Ciphergen® Q10 ProteinChip® array), a cation exchange adsorbent (such as the Ciphergen® CM10 ProteinChip® array) and a metal chelate adsorbent (such as the Ciphergen® IMAC-30 ProteinChip® array). A number of the biomarkers bind to a hydrophobic adsorbent (such as the Ciphergen® H50 ProteinChip® array) using a binding and washing buffer of 10% acetonitrile. Some of the biomarkers bind to an anion exchange adsorbent (such as the Ciphergen® Q10 ProteinChip® array) using a binding and washing buffer of 50 mM Tris buffer at pH 8.0. A number of the biomarkers bind to a metal chelate adsorbent (such as the Ciphergen® IMAC-30 ProteinChip® array coupled with copper) using, for example, a binding and washing buffer of 50 mM Tris pH 8.0/500 mM NaCl. Most of the biomarkers bind to cation exchange adsorbents (e.g., the Ciphergen® CM10 ProteinChip® array) after washing with 100 mM sodium acetate at pH 4.

The identity of certain of the biomarkers of this invention has been determined and is indicated in Table 1. The method by which this determination was made is described in the Example Section. For biomarkers whose identify has been determined, the presence of the biomarker can be determined by other methods known in the art (e.g., by immunoassay).

Because the biomarkers of this invention are characterized by mass-to-charge ratio, binding properties and spectral shape, they can be detected by mass spectrometry without knowing their specific identity. However, if desired, biomarkers whose identity is not determined can be identified by, for example, determining the amino acid sequence of the polypeptides. For example, a biomarker can be peptide-mapped with a number of enzymes, such as trypsin or V8 protease, and the molecular weights of the digestion fragments can be used to search databases for sequences that match the molecular weights of the digestion fragments generated by the various enzymes. Alternatively, protein biomarkers can be sequenced using tandem MS technology. In this method, the protein is isolated by, for example, gel electrophoresis. A band containing the biomarker is cut out and the protein is subject to protease digestion. Individual protein fragments are separated by a first mass spectrometer. The fragment is then subjected to collision-induced cooling, which fragments the peptide and produces a polypeptide ladder. A polypeptide ladder is then analyzed by the second mass spectrometer of the tandem MS. The difference in masses of the members of the polypeptide ladder identifies the amino acids in the sequence. An entire protein can be sequenced this way, or a sequence fragment can be subjected to database mining to find identity candidates.

The preferred biological source for detection of the biomarkers is ovarian cyst fluid. However, in other embodiments, the biomarkers are detected in other bodily fluids, e.g., serum, blood or urine.

The biomarkers of this invention are biomolecules. Accordingly, this invention provides these biomolecules in isolated form. The biomarkers can be isolated from biological fluids, such as urine or serum. They can be isolated by any method known in the art, based on both their mass and their binding characteristics. For example, a sample comprising the biomolecules can be subject to chromatographic fractionation, as described herein, and subject to further separation by, e.g., acrylamide gel electrophoresis. Knowledge of the identity of the biomarker also allows their isolation by immunoaffinity chromatography.

III. Biomarkers and Different Forms of a Protein

Proteins frequently exist in a sample in a plurality of different forms characterized by a detectably different mass. These forms can result from either or both of pre- and post-translational modification. Pre-translational modified forms include allelic variants, slice variants and RNA editing forms. Post-translationally modified forms include forms resulting from proteolytic cleavage (e.g., fragments of a parent protein), glycosylation, phosphorylation, lipidation, oxidation, methylation, cystinylation, sulphonation and acetylation. When detecting or measuring a protein in a sample, the ability to differentiate between different forms of a protein depends upon the nature of the difference and the method used to detect or measure. For example, an immunoassay using a monoclonal antibody will detect all forms of a protein containing the eptiope and will not distinguish between them. However, a sandwich immunoassay that uses two antibodies directed against different epitopes on a protein will detect all forms of the protein that contain both epitopes and will not detect those forms that contain only one of the epitopes. In diagnostic assays, the inability to distinguish different forms of a protein has little impact when the forms detected by the particular method used are equally good biomarkers as any particular form. However, when a particular form (or a subset of particular forms) of a protein is a better biomarker than the collection of different forms detected together by a particular method, the power of the assay may suffer. In this case, it is useful to employ an assay method that distinguishes between forms of a protein and that specifically detects and measures a desired form or forms of the protein. Distinguishing different forms of an analyte or specifically detecting a particular form of an analyte is referred to as "resolving" the analyte.

Mass spectrometry is a particularly powerful methodology to resolve different forms of a protein because the different forms typically have different masses that can be resolved by mass spectrometry. Accordingly, if one form of a protein is a superior biomarker for a disease than another form of the biomarker, mass spectrometry may be able to specifically detect and measure the useful form where traditional immunoassay fails to distinguish the forms and fails to specifically detect to useful biomarker.

One useful methodology combines mass spectrometry with immunoassay. First, a biospecific capture reagent (e.g., an antibody, aptamer or Affibody that recognizes the biomarker and other forms of it) is used to capture the biomarker of interest. Preferably, the biospecific capture reagent is bound to a solid phase, such as a bead, a plate, a membrane or an array. After unbound materials are washed away, the captured analytes are detected and/or measured by mass spectrometry. (This method also will also result in the capture of protein interactors that are bound to the proteins or that are otherwise recognized by antibodies and that, themselves, can be biomarkers.) Various forms of mass spectrometry are useful for detecting the protein forms, including laser desorption approaches, such as traditional MALDI or SELDI, and electrospray ionization.

Thus, when reference is made herein to detecting a particular protein or to measuring the amount of a particular protein, it means detecting and measuring the protein with or without resolving various forms of protein. For example, the step of "measuring Calgranulin C" includes measuring any and/or all forms of Calgranulin C by means that do not differentiate between various forms of the protein in a sample (e.g., certain immunoassays) as well as by means that differentiate some forms from other forms or that measure a specific form of the protein (e.g., mass spectrometry). In contrast, when it is desired to measure a particular form or forms of a protein (e.g., a particular form of Calgranulin C including forms modified by truncation, phosphorylation, glycosylation, etc.), the particular form (or forms) is specified. For example, "measuring M10430" means measuring a polypeptide having an apparent molecular weight of 10430 Da that, therefore, distinguishes M10430 from other forms of Calgranulin C.

IV. Detection of Biomarkers for Ovarian Cancer

The biomarkers of this invention can be detected by any suitable method. Detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

In one embodiment, a sample is analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there.

Protein biochips are biochips adapted for the capture of polypeptides. Many protein biochips are described in the art. These include, for example, protein biochips produced by Ciphergen Biosystems, Inc. (Fremont, Calif.), Zyomyx (Hayward, Calif.), Invitrogen (Carlsbad, Calif.), Biacore (Uppsala, Sweden) and Procognia (Berkshire, UK). Examples of such protein biochips are described in the following patents or published patent applications: U.S. Pat. No. 6,225,047 (Hutchens et al.); U.S. Pat. No. 6,537,749 (Kuimelis et al.); U.S. Pat. No. 6,329,209 (Wagner et al.); PCT International Publication No. WO 00/56934 (Englert et al.); PCT International Publication No. WO 03/048768 (Boutell et al.) and U.S. Pat. No. 5,242,828 (Bergstrom et al.).

Detection by Mass Spectrometry

In a preferred embodiment, the biomarkers of this invention are detected by mass spectrometry, a method that employs a mass spectrometer to detect gas phase ions. Examples of mass spectrometers are time-of-flight, magnetic sector, quadrupole filter, ion trap, ion cyclotron resonance, electrostatic sector analyzer and hybrids of these.

In a further preferred method, the mass spectrometer is a laser desorption/ionization mass spectrometer. In laser desorption/ionization mass spectrometry, the analytes are placed on the surface of a mass spectrometry probe, a device adapted to engage a probe interface of the mass spectrometer and to present an analyte to ionizing energy for ionization and introduction into a mass spectrometer. A laser desorption mass spectrometer employs laser energy, typically from an ultraviolet laser, but also from an infrared laser, to desorb analytes from a surface, to volatilize and ionize them and make them available to the ion optics of the mass spectrometer. The analysis of proteins by LDI can take the form of MALDI or of SELDI.

Laser desorption/ionization in a single TOF instrument typically is performed in linear extraction mode. Tandem mass spectrometers can employ orthogonal extraction modes.

SELDI

A preferred mass spectrometric technique for use in the invention is "Surface Enhanced Laser Desorption and Ionization" or "SELDI," as described, for example, in U.S. Pat. Nos. 5,719,060 and 6,225,047, both to Hutchens et al. This refers to a method of desorption/ionization gas phase ion spectrometry (e.g., mass spectrometry) in which an analyte (here, one or more of the biomarkers) is captured on the surface of a SELDI mass spectrometry probe. There are several versions of SELDI.

One version of SELDI is called "affinity capture mass spectrometry." It also is called "Surface-Enhanced Affinity Capture" or "SEAC." This version involves the use of probes that have a material on the probe surface that captures analytes through a non-covalent affinity interaction (adsorption) between the material and the analyte. The material is variously called an "adsorbent," a "capture reagent," an "affinity reagent" or a "binding moiety." Such probes can be referred to as "affinity capture probes" and as having an "adsorbent surface." The capture reagent can be any material capable of binding an analyte. The capture reagent is attached to the probe surface by physisorption or chemisorption. In certain embodiments the probes have the capture reagent already attached to the surface. In other embodiments, the probes are pre-activated and include a reactive moiety that is capable of binding the capture reagent, e.g., through a reaction forming a covalent or coordinate covalent bond. Epoxide and acyl-imidizole are useful reactive moieties to covalently bind polypeptide capture reagents such as antibodies or cellular receptors. Nitrilotriacetic acid and iminodiacetic acid are useful reactive moieties that function as chelating agents to bind metal ions that interact non-covalently with histidine containing peptides. Adsorbents are generally classified as chromatographic adsorbents and biospecific adsorbents.

"Chromatographic adsorbent" refers to an adsorbent material typically used in chromatography. Chromatographic adsorbents include, for example, ion exchange materials, metal chelators (e.g., nitrilotriacetic acid or iminodiacetic acid), immobilized metal chelates, hydrophobic interaction adsorbents, hydrophilic interaction adsorbents, dyes, simple biomolecules (e.g., nucleotides, amino acids, simple sugars and fatty acids) and mixed mode adsorbents (e.g., hydrophobic attraction/electrostatic repulsion adsorbents).

"Biospecific adsorbent" refers to an adsorbent comprising a biomolecule, e.g., a nucleic acid molecule (e.g., an aptamer), a polypeptide, a polysaccharide, a lipid, a steroid or a conjugate of these (e.g., a glycoprotein, a lipoprotein, a glycolipid, a nucleic acid (e.g., DNA)-protein conjugate). In certain instances, the biospecific adsorbent can be a macromolecular structure such as a multiprotein complex, a biological membrane or a virus. Examples of biospecific adsorbents are antibodies, receptor proteins and nucleic acids. Biospecific adsorbents typically have higher specificity for a target analyte than chromatographic adsorbents. Further examples of adsorbents for use in SELDI can be found in U.S. Pat. No. 6,225,047. A "bioselective adsorbent" refers to an adsorbent that binds to an analyte with an affinity of at least $10^{-8}$ M.

Protein biochips produced by Ciphergen Biosystems, Inc. comprise surfaces having chromatographic or biospecific adsorbents attached thereto at addressable locations. Ciphergen's ProteinChip® arrays include NP20 (hydrophilic); H4 and H50 (hydrophobic); SAX-2, Q-10 and LSAX-30 (anion exchange); WCX-2, CM-10 and LWCX-30 (cation exchange); IMAC-3, IMAC-30 and IMAC-50 (metal chelate); and PS-10, PS-20 (reactive surface with acyl-imidizole, epoxide) and PG-20 (protein G coupled through acyl-imidizole). Hydrophobic ProteinChip arrays have isopropyl or nonylphenoxy-poly(ethylene glycol)methacrylate functionalities. Anion exchange ProteinChip arrays have quaternary ammonium functionalities. Cation exchange ProteinChip arrays have carboxylate functionalities. Immobilized metal chelate ProteinChip arrays have nitrilotriacetic acid functionalities (IMAC-3 and IMAC-30) or O-methacryloyl-N,N-biscarboxymethyl tyrosine functionalities (IMAC-50) that adsorb transition metal ions, such as copper, nickel, zinc, and gallium, by chelation. Preactivated ProteinChip arrays have acyl-imidizole or epoxide functional groups that can react with groups on proteins for covalent binding.

Such biochips are further described in: U.S. Pat. No. 6,579,719 (Hutchens et al., "Retentate Chromatography," Jun. 17, 2003); U.S. Pat. No. 6,897,072 (Rich et al., "Probes for a Gas Phase Ion Spectrometer," May 24, 2005); U.S. Pat. No. 6,555,813 (Beecher et al., "Sample Holder with Hydrophobic Coating for Gas Phase Mass Spectrometer," Apr. 29, 2003); U.S. Patent Publication No. U.S. 2003 0032043 A1 (Pohl et al., "Latex Based Adsorbent Chip," Jul. 16, 2002); PCT International Publication No. WO 03/040700 (Um et al., "Hydrophobic Surface Chip," May 15, 2003); U.S. Patent Publication No. US 2003/0218130 A1 (Boschetti et al., "Biochips With Surfaces Coated With Polysaccharide-Based Hydrogels," Apr. 14, 2003) and U.S. Pat. No. 7,045,366 (Huang et al., "Photocrosslinked Hydrogel Surface Coatings," May 16, 2006).

In general, a probe with an adsorbent surface is contacted with the sample for a period of time sufficient to allow the biomarker or biomarkers that may be present in the sample to bind to the adsorbent. After an incubation period, the substrate is washed to remove unbound material. Any suitable washing solutions can be used; preferably, aqueous solutions are employed. The extent to which molecules remain bound can be manipulated by adjusting the stringency of the wash. The elution characteristics of a wash solution can depend, for example, on pH, ionic strength, hydrophobicity, degree of chaotropism, detergent strength, and temperature. Unless the probe has both SEAC and SEND properties (as described herein), an energy absorbing molecule then is applied to the substrate with the bound biomarkers.

In yet another method, one can capture the biomarkers with a solid-phase bound immuno-adsorbent that has antibodies that bind the biomarkers. After washing the adsorbent to remove unbound material, the biomarkers are eluted from the solid phase, applied to a SELDI biochip that binds the biomarkers and analyzed by SELDI.

The biomarkers bound to the substrates are detected in a gas phase ion spectrometer such as a time-of-flight mass spectrometer. The biomarkers are ionized by an ionization source such as a laser, the generated ions are collected by an ion optic assembly, and then a mass analyzer disperses and analyzes the passing ions. The detector then translates information of the detected ions into mass-to-charge ratios. Detection of a biomarker typically will involve detection of signal intensity. Thus, both the quantity and mass of the biomarker can be determined.

SEND

Another method of laser desorption mass spectrometry is called Surface-Enhanced Neat Desorption ("SEND"). SEND involves the use of probes comprising energy absorbing molecules that are chemically bound to the probe surface ("SEND probe"). The phrase "energy absorbing molecules" (EAM) denotes molecules that are capable of absorbing energy from a laser desorption/ionization source and, thereafter, contribute to desorption and ionization of analyte molecules in contact therewith. The EAM category includes molecules used in MALDI, frequently referred to as "matrix," and is exemplified by cinnamic acid derivatives, sinapinic acid (SPA), cyano-hydroxy-cinnamic acid (CHCA) and dihydroxybenzoic acid, ferulic acid, and hydroxyaceto-phenone derivatives. In certain embodiments, the energy absorbing molecule is incorporated into a linear or cross-linked polymer, e.g., a polymethacrylate. For example, the composition can be a co-polymer of α-cyano-4-methacryloyloxycinnamic acid and acrylate. In another embodiment, the composition is a co-polymer of α-cyano-4-methacryloyloxycinnamic acid, acrylate and 3-(tri-ethoxy)silyl propyl methacrylate. In another embodiment, the composition is a co-polymer of α-cyano-4-methacryloyloxycinnamic acid and octadecyl-methacrylate ("C18 SEND"). SEND is further described in U.S. Pat. No. 6,124,137 and PCT International Publication No. WO 03/64594 (Kitagawa, "Monomers And Polymers Having Energy Absorbing Moieties of Use In Desorption/Ionization Of Analytes," Aug. 7, 2003).

SEAC/SEND is a version of SELDI in which both a capture reagent and an energy absorbing molecule are attached to the sample presenting surface. SEAC/SEND probes therefore allow the capture of analytes through affinity capture and ionization/desorption without the need to apply external matrix. The C18 SEND biochip is a version of SEAC/SEND, comprising a C18 moiety which functions as a capture reagent, and a CHCA moiety which functions as an energy absorbing moiety.

SEPAR

Another version of LDI is called Surface-Enhanced Photolabile Attachment and Release ("SEPAR"). SEPAR involves the use of probes having moieties attached to the surface that can covalently bind an analyte, and then release the analyte through breaking a photolabile bond in the moiety after exposure to light, e.g., to laser light (see, U.S. Pat. No. 5,719,060). SEPAR and other forms of SELDI are readily adapted to detecting a biomarker or biomarker profile, pursuant to the present invention.

MALDI

MALDI is a traditional method of laser desorption/ionization used to analyte biomolecules such as proteins and nucleic acids. In one MALDI method, the sample is mixed with matrix and deposited directly on a MALDI array. However, the complexity of biological samples such as serum and urine makes this method less than optimal without prior fractionation of the sample. Accordingly, in certain embodiments with biomarkers are preferably first captured with biospecific (e.g., an antibody) or chromatographic materials coupled to a solid support such as a resin (e.g., in a spin column). Specific affinity materials that bind the biomarkers of this invention are described above. After purification on the affinity material, the biomarkers are eluted and then detected by MALDI.

In another mass spectrometry method, the biomarkers are first captured on a chromatographic resin having chromatographic properties that bind the biomarkers. In the present example, this could include a variety of methods. For example, one could capture the biomarkers on a cation exchange resin, such as CM Ceramic HyperD F resin, wash the resin, elute the biomarkers and detect by MALDI. Alternatively, this method could be preceded by fractionating the sample on an anion exchange resin before application to the cation exchange resin. In another alternative, one could fractionate on an anion exchange resin and detect by MALDI directly. In yet another method, one could capture the biomarkers on an immuno-chromatographic resin that comprises antibodies that bind the biomarkers, wash the resin to remove unbound material, elute the biomarkers from the resin and detect the eluted biomarkers by MALDI or by SELDI.

Other Forms of Ionization in Mass Spectrometry

In another method, the biomarkers are detected by LC-MS or LC-LC-MS. This involves resolving the proteins in a sample by one or two passes through liquid chromatography, followed by mass spectrometry analysis, typically electrospray ionization.

Data Analysis

Analysis of analytes by time-of-flight mass spectrometry generates a time-of-flight spectrum. The time-of-flight spectrum ultimately analyzed typically does not represent the signal from a single pulse of ionizing energy against a sample, but rather the sum of signals from a number of pulses. This reduces noise and increases dynamic range. This time-of-flight data is then subject to data processing. In Ciphergen's ProteinChip® software, data processing typically includes TOF-to-M/Z transformation to generate a mass spectrum, baseline subtraction to eliminate instrument offsets and high frequency noise filtering to reduce high frequency noise.

Data generated by desorption and detection of biomarkers can be analyzed with the use of a programmable digital computer. The computer program analyzes the data to indicate the number of biomarkers detected, and optionally the strength of the signal and the determined molecular mass for each biomarker detected. Data analysis can include steps of determining signal strength of a biomarker and removing data deviating from a predetermined statistical distribution. For example, the observed peaks can be normalized, by calculating the height of each peak relative to some reference.

The computer can transform the resulting data into various formats for display. The standard spectrum can be displayed, but in one useful format only the peak height and mass information are retained from the spectrum view, yielding a cleaner image and enabling biomarkers with nearly identical molecular weights to be more easily seen. In another useful format, two or more spectra are compared, conveniently highlighting unique biomarkers and biomarkers that are up- or down-regulated between samples. Using any of these formats, one can readily determine whether a particular biomarker is present in a sample.

Analysis generally involves the identification of peaks in the spectrum that represent signal from an analyte. Peak selection can be done visually, but software is available, as part of Ciphergen's ProteinChip® software package, that can automate the detection of peaks. In general, this software functions by identifying signals having a signal-to-noise ratio above a selected threshold and labeling the mass of the peak at the centroid of the peak signal. In one useful application, many spectra are compared to identify identical peaks present in some selected percentage of the mass spectra. One version of this software clusters all peaks appearing in the various spectra within a defined mass range, and assigns a mass (M/Z) to all the peaks that are near the mid-point of the mass (M/Z) cluster.

Software used to analyze the data can include code that applies an algorithm to the analysis of the signal to determine whether the signal represents a peak in a signal that corresponds to a biomarker according to the present invention. The software also can subject the data regarding observed biomarker peaks to classification tree or ANN analysis, to determine whether a biomarker peak or combination of biomarker peaks is present that indicates the status of the particular clinical parameter under examination. Analysis of the data may be "keyed" to a variety of parameters that are obtained, either directly or indirectly, from the mass spectrometric analysis of the sample. These parameters include, but are not limited to, the presence or absence of one or more peaks, the shape of a peak or group of peaks, the height of one or more peaks, the log of the height of one or more peaks, and other arithmetic manipulations of peak height data.

General Protocol for SELDI Detection of Biomarkers for Ovarian Cancer

Typically, the biological sample to be tested, e.g., ovarian cyst fluid, is subject to pre-treatment before SELDI analysis. For example, a prefractionation step often simplifies the sample and improves sensitivity. The Example presented herein provides several possible methods of selectively binding, washing and eluting biomarkers found in ovarian cyst fluid. For eluting, the bound materials are typically subjected to stepwise pH elutions using buffers, e.g., at pH 9, pH 7, pH 5, pH 4, etc. (The fractions in which the biomarkers of Table 1 are eluted are indicated in the Table). Various fractions containing the biomarker are collected. In another embodiment (e.g., the Standard Profiling Method in Example 1), the biological sample to be tested, e.g., ovarian cyst fluid samples, is not subject to a pre-fractionation step, but is used in the chip binding step unfractionated. Example 1 also provides an Immunoprecipitation Method and a method which employs tandem Equalizer beads and Mercapto Ethyl Pyridine (MEP) beads.

The sample to be tested (either unfractionated or pre-fractionated) is then contacted with an affinity capture probe. Examples of affinity capture probes of chromatographic surfaces that the biomarkers of this invention bind include, but are not limited to, a hydrophobic adsorbent (such as the Ciphergen® H50 ProteinChip® array), an anion exchange adsorbent (such as the Ciphergen® Q10 ProteinChip® array), a cation exchange adsorbent (such as the Ciphergen® CM10 ProteinChip® array) and a metal chelate adsorbent (such as the Ciphergen® IMAC-30 ProteinChip® array). The probe is washed with a buffer that will retain the biomarker while washing away unbound molecules, as described in the Examples. The biomarkers are detected by laser desorption/ionization mass spectrometry.

Alternatively, samples may be diluted, with or without denaturing, in the appropriate array binding buffer and bound and washed under conditions optimized for detecting each analyte.

Alternatively, if antibodies that recognize the biomarker are available, for example in the case of Apolipoprotein C1 (ApoC1), hemoglobin alpha, hemoglobin beta, Apolipoprotein AII (ApoAII), Apolipoprotein CII (ApoCII), Calgranulin C (both full-length and truncated form), Calgranulin A, IgG heavy chain, Calcyclin and Transthyretin, these can be attached to the surface of a probe, such as a pre-activated PS10 or PS20 ProteinChip array (Ciphergen Biosystems, Inc.). These antibodies can capture the biomarkers from a sample onto the probe surface. Then the biomarkers can be detected by, e.g., laser desorption/ionization mass spectrometry.

Any robot that performs fluidics operations can be used in these assays, for example, those available from Hewlett Packard and Hamilton.

Detection by Immunoassay

In another embodiment of the invention, the biomarkers of the invention are measured by a method other than mass spectrometry or methods that rely on a measurement of the mass of the biomarker. In another embodiment, the biomarkers of this invention are measured by immunoassay. Immunoassay requires biospecific capture reagents, such as antibodies, to capture the biomarkers. Antibodies can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well known in the art.

This invention contemplates traditional immunoassays including, for example, sandwich immunoassays including ELISA or fluorescence-based immunoassays, as well as other enzyme immunoassays. Nephelometry is an assay done in liquid phase, in which antibodies are in solution. Binding of the antigen to the antibody results in changes in absorbance, which is measured. In the SELDI-based immunoassay, a biospecific capture reagent for the biomarker is attached to the surface of an MS probe, such as a pre-activated ProteinChip array. The biomarker is then specifically captured on the biochip through this reagent, and the captured biomarker is detected by mass spectrometry.

V. Determination of Subject Ovarian Cancer Status

The biomarkers of the invention can be used in diagnostic tests to assess ovarian cancer status in a subject, e.g., to diagnose ovarian cancer. The phrase "ovarian cancer status" includes any distinguishable manifestation of the disease. For example, ovarian cancer disease status includes, without limitation, the presence or absence of disease (e.g., ovarian cancer (malignant) versus ovarian cancer of low malignant potential versus benign ovarian disease versus other malignant conditions), the risk of developing disease, the stage of the disease, the progress of disease (e.g., progress of disease or remission of disease over time) and the effectiveness or response to treatment of disease. Based on this status, further procedures may be indicated, including additional diagnostic tests or therapeutic procedures or regimens.

The correlation of test results with ovarian cancer status applying a classification algorithm of some kind to the results to generate the status. The classification algorithm may be as simple as determining whether or not the amount of a given biomarker measured is above or below a particular cut-off number. When multiple biomarkers are used, the classification algorithm may be a linear regression formula. Alternatively, the classification algorithm may be the product of any of a number of learning algorithms described herein.

In the case of complex classification algorithms, it may be necessary to perform the algorithm on the data, thereby determining the classification, using a computer, e.g., a programmable digital computer. In either case, one can then record the status on tangible medium, for example, in computer-readable format such as a memory drive or disk or simply printed on paper. The result also could be reported on a computer screen.

Single Markers

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

The biomarkers of this invention show a statistical difference in different ovarian cancer statuses of at least $p \leq 0.05$, $p \leq 10^{-2}$, $p \leq \leq 10^{-3}$, $p \leq 10^{-4}$ or $p \leq 10^{-5}$. Diagnostic tests that use these biomarkers alone or in combination show a sensitivity and specificity of at least 75%, at least 80%, at least 85%, at least 90%, at least 95%, at least 98% and about 100%.

Each biomarker listed in Table 1 is differentially present in ovarian cancer (malignant), in ovarian cancer LMP, in benign ovarian disease or in other malignant conditions), and, therefore, each is individually useful in aiding in the determination of ovarian cancer status. The method involves, first, measuring the selected biomarker in a subject sample using the methods described herein, e.g., capture on a SELDI biochip followed by detection by mass spectrometry and, second, comparing the measurement with a diagnostic amount or cut-off that distinguishes a positive ovarian cancer status from a negative ovarian cancer status. The diagnostic amount represents a measured amount of a biomarker above which or below which a subject is classified as having a particular ovarian cancer status. For example, if the biomarker is up-regulated compared to normal during ovarian cancer, then a measured amount above the diagnostic cutoff provides a diagnosis of ovarian cancer. Alternatively, if the biomarker is down-regulated during ovarian cancer, then a measured amount below the diagnostic cutoff provides a diagnosis of ovarian cancer. As is well understood in the art, by adjusting the particular diagnostic cut-off used in an assay, one can increase sensitivity or specificity of the diagnostic assay depending on the preference of the diagnostician. The particular diagnostic cut-off can be determined, for example, by measuring the amount of the biomarker in a statistically significant number of samples from subjects with the different ovarian cancer statuses, as was done here, and drawing the cut-off to suit the diagnostician's desired levels of specificity and sensitivity.

Combinations of Markers

While individual biomarkers are useful diagnostic biomarkers, it has been found that a combination of biomarkers can provide greater predictive value of a particular status than single biomarkers alone. Specifically, the detection of a plurality of biomarkers in a sample can increase the sensitivity and/or specificity of the test. A combination of at least two biomarkers is sometimes referred to as a "biomarker profile" or "biomarker fingerprint." A combination of the biomarkers set forth in Table 1 can be detected. Similarly, one or more of the biomarkers set forth in Table 1 can be detected in combination with other known ovarian cancer biomarkers, such as CA125. Examples of known ovarian cancer biomarkers useful in combination with the biomarkers of the present invention include, but are not limited to, those set forth in PCT Publications Nos. WO 2003/057014, WO 2004/012588, and WO 2007/002535, each of which are incorporated herein by reference for all purposes.

The protocols described in the Examples below were used to generate mass spectra from 187 samples of which 58 were obtained from patients diagnosed with malignant ovarian cancer (the remaining were samples from patients with benign ovarian disease). The peak masses and heights can be abstracted into a discovery data set. This data set can then be used to train a learning algorithm employing classification and regression tree analysis (CART) (Ciphergen Biomarker Patterns Software™). Among the many decision trees generated by CART, those with excellent sensitivity and specificity in distinguishing malignant ovarian cancer from benign ovarian disease will be most useful for practitioners.

It is also noted that the specifics of the decision trees, in particular the cut-off values used in making branching decisions, depends on the details of the assay used to generate the discovery data set. In developing a classification algorithm from, for example, a new sample set or a different assay protocol, the operator uses a protocol that detects these biomarkers and keys the learning algorithm to include them.

Also, a diagnostic test for ovarian cancer status involving the measurement of any biomarker of this invention may include any of the following biomarkers for ovarian cancer identified in Table 2 (including their modified forms where appropriate):

TABLE 2

| Marker | Comments (up- or down-regulated in cancer) |
|---|---|
| CTAP3 | Up-regulated; 9293D<br>IMAC-Cu 100 mM Na phosphate, pH 7.0 |
| Transferrin | Down-regulated; 79 kD, detected on IMAC ProteinChip array charged with nickel<br>WO 03/057014 |
| Haptoglobin precursor protein fragment | Up-regulated; 9.2 kD detected on IMAC ProteinChip array charged with nickel<br>WO 03/057014 |
| ApoA1 | Down-regulated; predicted mass 28078.62D; detected on IMAC or H50 ProteinChip array.<br>WO 2004/013609 |
| Transthyretin and transthyretin delta N 10 | Down-regulated; predicted mass 13761D and 12887 D, respectively; detected on Q10 ProteinChip array.<br>WO 2004/013609 |
| ITIH4 internal fragments | Up-regulated; among other fragments: MNFRPGVLSSRQLGLPGPPDVPDHAAYHPF (SEQ ID NO: 1), a fragment spanning amino acids 660-689 of human Inter-alpha trypsin inhibitor, heavy chain H4, predicted mass: 3273.72 D; detected on IMAC ProteinChip array<br>WO 2004/013609 and WO 2005/098447 |
| Beta 2-microglobulin | Up-regulated; detected at 11.7 KD on IMAC-Cu<br>ProteinChip array<br>US Provisional Application 60/693,679, filed<br>Jun. 24, 2005 |
| Hepcidin and modified forms | Up-regulated; detected by SELDI-co-precipitate with ITIH4 fragment.<br>Hepcidin-25 (SEQ ID NO: 2):<br>DTHFPICIFCCGCCHRSKCGMCCKT<br>Hepcidin-24 (SEQ ID NO: 3):<br>THFPICIFCCGCCHRSKCGMCCKT<br>Hepcidin-22 (SEQ ID NO: 5):<br>FPICIFCCGCCHRSKCGM CCKT<br>Hepcidin-20 (SEQ ID NO: 4):<br>ICIFCCGCCHRSKCGMCCKT |
| Haptoglobin alpha | Up-regulated. Detected at 11,600D-11,700D on an IMAC ProteinChip array charged with copper;<br>WO 02/100242 |
| Prostatin | Up-regulated<br>U.S. Pat. No. 6,846,642 |
| Osteopontin | Up-regulated<br>In urine-Glycosylated--US 2005-0009 120 A1<br>In serum-US 2005-0214826 |
| Eosinophil-derived neurotoxin | Up regulated in urine. Glycosylated Detected at 17.4 KDa on a WCX2 ProteinChip array.<br>US 2005-0009120 A1 |
| leptin | Down-regulated;<br>US 2005-0214826 |
| prolactin | Up-regulated;<br>US 2005-0214826 |
| IGF-II | Down-regulated;<br>US 2005-0214826 |
| Hemoglobin (alpha-hemoglobin, beta-hemoglobin) | Up-regulated;<br>WO 2006-019906 |
| CA 125 | Up-regulated |

Other biomarkers with which the biomarkers of the present invention can be combined include, but are not limited to, CTAP3, CA125 II, CA15-3, CA19-9, CA72-4, CA 195, tumor associated trypsin inhibitor (TATI), CEA, placental alkaline phosphatase (PLAP), Sialyl TN, galactosyltransferase, macrophage colony stimulating factor (M-CSF, CSF-1), lysophosphatidic acid (LPA), 110 kD component of the extracellular domain of the epidermal growth factor receptor (p110EGFR), tissue kallikreins, e.g., kallikrein 6 and kallikrein 10 (NES-1), prostasin, E4, creatine kinase B (CKB), LASA, HER-2/neu, urinary gonadotropin peptide, Dianon NB 70/K, Tissue peptide antigen (TPA), SMRP, osteopontin, and haptoglobin, leptin, prolactin, insulin like growth factor I or II.

Ovarian Cancer Status

Determining ovarian cancer status typically involves classifying an individual into one of two or more groups (statuses) based on the results of the diagnostic test. The diagnostic tests described herein can be used to classify between a number of different states.

Presence of Ovarian Cancer

In one embodiment, this invention provides methods for determining the presence of ovarian cancer in a subject (status: ovarian cancer versus ovarian cancer of low malignant potential or benign ovarian disease). The presence or absence of ovarian cancer is determined by measuring the relevant biomarker or biomarkers and then either submitting them to a classification algorithm or comparing them with a reference amount and/or pattern of biomarkers that is associated with the particular risk level.

Determining Risk of Developing Disease

In one embodiment, this invention provides methods for determining the risk of developing disease in a subject. Biomarker amounts or patterns are characteristic of various risk states, e.g., high, medium or low. The risk of developing a disease is determined by measuring the relevant biomarker or biomarkers and then either submitting them to a classification algorithm or comparing them with a reference amount and/or pattern of biomarkers that is associated with the particular risk level.

Determining Stage of Disease

In one embodiment, this invention provides methods for determining the stage of disease in a subject. Each stage of the disease has a characteristic amount of a biomarker or relative amounts of a set of biomarkers (a pattern). The stage of a disease is determined by measuring the relevant biomarker or biomarkers and then either submitting them to a classification algorithm or comparing them with a reference amount and/or pattern of biomarkers that is associated with the particular stage. For example, one can classify between early stage ovarian cancer and non-ovarian cancer or among stage I ovarian cancer, stage II ovarian cancer and stage III ovarian cancer.

Determining Course (Progression/Remission) of Disease

In one embodiment, this invention provides methods for determining the course of disease in a subject. Disease course refers to changes in disease status over time, including disease progression (worsening) and disease regression (improvement). Over time, the amounts or relative amounts (e.g., the pattern) of the biomarkers changes. Therefore, the trend of these markers, either increased or decreased over time toward diseased or non-diseased indicates the course of the disease. Accordingly, this method involves measuring one or more biomarkers in a subject at least two different time points, e.g., a first time and a second time, and comparing the change in amounts, if any. The course of disease is determined based on these comparisons.

Similarly, changes in the rate of disease progression (or regression) may be monitored by measuring the amount of a biomarker, e.g., a peptide biomarkers of Table 1, at different times and calculating the rate of change in biomarker levels. The ability to measure disease state or velocity of disease progression can be important for drug treatment studies where the goal is to slow down or arrest disease progression through therapy.

Reporting the Status

Additional embodiments of the invention relate to the communication of assay results or diagnoses or both to technicians, physicians or patients, for example. In certain embodiments, computers will be used to communicate assay results or diagnoses or both to interested parties, e.g., physicians and their patients. In some embodiments, the assays will be performed or the assay results analyzed in a country or jurisdiction which differs from the country or jurisdiction to which the results or diagnoses are communicated.

In a preferred embodiment of the invention, a diagnosis based on the differential presence in a test subject of any of the peptide biomarkers of Table 1 is communicated to the subject as soon as possible after the diagnosis is obtained. The diagnosis may be communicated to the subject by the subject's treating physician. Alternatively, the diagnosis may be sent to a test subject by email or communicated to the subject by phone. A computer may be used to communicate the diagnosis by email or phone. In certain embodiments, the message containing results of a diagnostic test may be generated and delivered automatically to the subject using a combination of computer hardware and software which will be familiar to artisans skilled in telecommunications. One example of a healthcare-oriented communications system is described in U.S. Pat. No. 6,283,761; however, the present invention is not limited to methods which utilize this particular communications system. In certain embodiments of the methods of the invention, all or some of the method steps, including the assaying of samples, diagnosing of diseases, and communicating of assay results or diagnoses, may be carried out in diverse (e.g., foreign) jurisdictions.

Subject Management

In certain embodiments of the methods of qualifying ovarian cancer status, the methods further comprise managing subject treatment based on the status. Such management includes the actions of the physician or clinician subsequent to determining ovarian cancer status. For example, if a physician makes a diagnosis of ovarian cancer, then a certain regime of treatment, such as prescription or administration of an anti-chemotherapeutic agent might follow. Alternatively, a diagnosis of ovarian cancer LMP or benign ovarian disease might be followed with further testing to determine a specific disease that might the patient might be suffering from. Also, if the diagnostic test gives an inconclusive result on ovarian cancer status, further tests may be called for.

Additional embodiments of the invention relate to the communication of assay results or diagnoses or both to technicians, physicians or patients, for example. In certain embodiments, computers will be used to communicate assay results or diagnoses or both to interested parties, e.g., physicians and their patients. In some embodiments, the assays will be performed or the assay results analyzed in a country or jurisdiction which differs from the country or jurisdiction to which the results or diagnoses are communicated.

In a preferred embodiment of the invention, a diagnosis based on the presence or absence in a test subject of any the biomarkers of Table 1 is communicated to the subject as soon as possible after the diagnosis is obtained. The diagnosis may be communicated to the subject by the subject's treating physician. Alternatively, the diagnosis may be sent to a test subject by email or communicated to the subject by phone. A computer may be used to communicate the diagnosis by email or phone. In certain embodiments, the message containing results of a diagnostic test may be generated and delivered automatically to the subject using a combination of computer hardware and software which will be familiar to artisans skilled in telecommunications. One example of a healthcare-oriented communications system is described in U.S. Pat. No. 6,283,761; however, the present invention is not limited to methods which utilize this particular communications system. In certain embodiments of the methods of the invention, all or some of the method steps, including the assaying of samples, diagnosing of diseases, and communicating of assay results or diagnoses, may be carried out in diverse (e.g., foreign) jurisdictions.

VI. Determining Therapeutic Efficacy of Pharmaceutical Drug

In another embodiment, this invention provides methods for determining the therapeutic efficacy of a pharmaceutical drug. These methods are useful in performing clinical trials of the drug, as well as monitoring the progress of a patient on the drug. Therapy or clinical trials involve administering the drug in a particular regimen. The regimen may involve a single dose of the drug or multiple doses of the drug over time. The doctor or clinical researcher monitors the effect of the drug on the patient or subject over the course of administration. If the drug has a pharmacological impact on the condition, the amounts or relative amounts (e.g., the pattern or profile) of the biomarkers of this invention changes toward a non-disease profile. For example, biomarker ApoCIII is increased with disease. Therefore, one can track the changes in the amount of this biomarker in the subject during the course of treatment. Accordingly, this method involves measuring one or more biomarkers in a subject receiving drug therapy, and correlating the amounts of the biomarkers with the disease status of the subject. One embodiment of this method involves determining the levels of the biomarkers at least two different time points during a course of drug therapy, e.g., a first time and a second time, and comparing the change in amounts of the biomarkers, if any. For example, the biomarkers can be measured before and after drug administration or at two different time points during drug administration. The effect of therapy is determined based on these comparisons. If a treatment is effective, then the biomarkers will trend toward normal, while if treatment is ineffective, the biomarkers will trend toward disease indications. If a treatment is effective, then the biomarkers will trend toward normal, while if treatment is ineffective, the biomarkers will trend toward disease indications.

VII. Generation of Classification Algorithms for Qualifying Ovarian Cancer Status In some embodiments, data derived from the spectra (e.g., mass spectra or time-of-flight spectra) that are generated using samples such as "known samples" can then be used to "train" a classification model. A "known sample" is a sample that has been pre-classified. The data that are derived from the spectra and are used to form the classification model can be referred to as a "training data set." Once trained, the classification model can recognize patterns in data derived from spectra generated using unknown samples. The classification model can then be used to classify the unknown samples into classes. This can be useful, for example, in predicting whether or not a particular biological sample is associated with a certain biological condition (e.g., diseased versus non-diseased).

The training data set that is used to form the classification model may comprise raw data or pre-processed data. In some embodiments, raw data can be obtained directly from time-of-flight spectra or mass spectra, and then may be optionally "pre-processed" as described above.

Classification models can be formed using any suitable statistical classification (or "learning") method that attempts to segregate bodies of data into classes based on objective parameters present in the data. Classification methods may be either supervised or unsupervised. Examples of supervised and unsupervised classification processes are described in Jain, "Statistical Pattern Recognition: A Review," *IEEE Transactions on Pattern Analysis and Machine Intelligence*, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART—classification and regression trees), artificial neural networks such as back propagation networks, discriminant analyses (e.g., Bayesian classifier or Fischer analysis), logistic classifiers, and support vector classifiers (support vector machines).

A preferred supervised classification method is a recursive partitioning process. Recursive partitioning processes use recursive partitioning trees to classify spectra derived from unknown samples. Further details about recursive partitioning processes are provided in U.S. Patent Application No. 2002/0138208 A1 to Paulse et al., "Method for Analyzing Mass Spectra."

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and Devices for Identifying Patterns in Biological Systems and Methods of Use Thereof"), U.S. Patent Application No. 2002 0193950 A1 (Gavin et al., "Method or analyzing mass spectra"), U.S. Patent Application No. 2003 0004402 A1 (Hitt et al., "Process for Discriminating Between Biological States Based on Hidden Patterns from Biological Data"), and U.S. Patent Application No. 2003 0055615 A1 (Zhang et al., "Systems and Methods for Processing Biological Expression Data").

The classification models can be formed on and used on any suitable digital computer. Suitable digital computers include micro, mini, or large computers using any standard or specialized operating system, such as a Unix, Windows™ or Linux™ based operating system. The digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including C, C++, visual basic, etc.

The learning algorithms described above are useful both for developing classification algorithms for the biomarkers already discovered, or for finding new biomarkers for ovarian cancer. The classification algorithms, in turn, form the base for diagnostic tests by providing diagnostic values (e.g., cut-off points) for biomarkers used singly or in combination.

VIII. Use of Biomarkers for Imaging

Non-invasive medical imaging techniques such as Positron Emisson Tomography (PET) or single photon emission computerized tomography (SPECT) imaging are particularly useful for the detection of cancer, coronary artery disease and brain disease. PET and SPECT imaging shows the chemical functioning of organs and tissues, while other imaging techniques—such as X-ray, CT and MRI—show structure. The use of PET and SPECT imaging has become increasingly useful for qualifying and monitoring the development of brain diseases such as Alzheimer's disease. In some instances, the use of PET or SPECT imaging allows Alzheimer's disease to be detected several years earlier than the onset of symptoms. See, e.g., Vassaux and Groot-wassink, "In Vivo Noninvasive Imaging for Gene Therapy," J. Biomedicine and Biotechnology, 2: 92-101 (2003).

Different strategies are being used to develop compounds suitable for in vivo imaging of amyloid deposits in human brains. Monoclonal antibodies against A-beta and peptide fragments have had limited uptake by the brain when tested in patients with AD. The small molecular approach for amyloid imaging has so far been most successful, as described by, e.g., Nordberg A, Lancet Neurol., 3(9):519-27 (2004); Kung M P et al, Brain Res., 1025(1-2):98-105 (2004); Herholz K et al., Mol Imaging Biol., 6(4):239-69 (2004); Neuropsychol Rev., Zakzanis K K et al., 13(1):1-18 (2003); Herholz K, Ann Nucl Med., 17(2):79-89 (2003).

The peptide biomarkers disclosed herein, or fragments thereof, can be used in the context of PET and SPECT imaging applications. After modification with appropriate tracer residues for PET or SPECT applications, peptide biomarkers which interact with amyloid plaque proteins can be used to image the deposition of amyloid plaques in Alzheimer's patients.

Antisense technology may be used to detect expression of transcripts whose translation is correlated with the biomarkers identified herein. For example, the use of antisense peptide nucleic acid (PNA) labeled with an appropriate radionuclide, such as $^{111}$In, and conjugated to a brain drug-targeting system to enable transport across biologic membrane barriers, has been demonstrated to allow imaging of endogenous gene expression in brain cancer. See Suzuki et al., Journal of Nuclear Medicine, 10:1766-1775 (2004). Suzuki et al. utilize a delivery system comprising monoclonal antibodies that target transferring receptors at the blood-brain barrier and facilitate transport of the PNA across that barrier.

IX. Compositions of Matter

In another aspect, this invention provides compositions of matter based on the biomarkers of this invention.

In one embodiment, this invention provides biomarkers of this invention in purified form. Purified biomarkers have utility as antigens to raise antibodies. Purified biomarkers also have utility as standards in assay procedures. As used herein, a "purified biomarker" is a biomarker that has been isolated from other proteins and peptides, and/or other material from the biological sample in which the biomarker is found. Biomarkers may be purified using any method known in the art, including, but not limited to, mechanical separation (e.g., centrifugation), ammonium sulphate precipitation, dialysis (including size-exclusion dialysis), size-exclusion chromatography, affinity chromatography, anion-exchange chromatography, cation-exchange chromatography, and methal-chelate chromatography. Such methods may be performed at any appropriate scale, for example, in a chromatography column, or on a biochip.

In another embodiment, this invention provides a biospecific capture reagent, optionally in purified form, that specifically binds a biomarker of this invention. In one embodiment, the biospecific capture reagent is an antibody. Such compositions are useful for detecting the biomarker in a detection assay, e.g., for diagnostics.

In another embodiment, this invention provides an article comprising a biospecific capture reagent that binds a biomarker of this invention, wherein the reagent is bound to a solid phase. For example, this invention contemplates a device comprising bead, chip, membrane, monolith or microtiter plate derivatized with the biospecific capture reagent. Such articles are useful in biomarker detection assays.

In another aspect this invention provides a composition comprising a biospecific capture reagent, such as an antibody, bound to a biomarker of this invention, the composition optionally being in purified form. Such compositions are useful for purifying the biomarker or in assays for detecting the biomarker.

In another embodiment, this invention provides an article comprising a solid substrate to which is attached an adsorbent, e.g., a chromatographic adsorbent or a biospecific capture reagent, to which is further bound a biomarker of this invention. In one embodiment, the article is a biochip or a probe for mass spectrometry, e.g., a SELDI probe. Such articles are useful for purifying the biomarker or detecting the biomarker.

X. Kits for Detection of Biomarkers for Ovarian Cancer

In another aspect, the present invention provides kits for qualifying ovarian cancer status, which kits are used to detect biomarkers according to the invention. In one embodiment, the kit comprises a solid support, such as a chip, a microtiter plate or a bead or resin having a capture reagent attached thereon, wherein the capture reagent binds a biomarker of the invention. Thus, for example, the kits of the present invention can comprise mass spectrometry probes for SELDI, such as ProteinChip® arrays. In the case of biospecific capture reagents, the kit can comprise a solid support with a reactive surface, and a container comprising the biospecific capture reagent.

The kit can also comprise a washing solution or instructions for making a washing solution, in which the combination of the capture reagent and the washing solution allows capture of the biomarker or biomarkers on the solid support for subsequent detection by, e.g., mass spectrometry. The kit may include more than type of adsorbent, each present on a different solid support.

In a further embodiment, such a kit can comprise instructions for suitable operational parameters in the form of a label or separate insert. For example, the instructions may inform a consumer about how to collect the sample, how to wash the probe or the particular biomarkers to be detected.

In yet another embodiment, the kit can comprise one or more containers with biomarker samples, to be used as standard(s) for calibration.

XI. Use of Biomarkers for Ovarian Cancer in Screening Assays and Methods of Treating Ovarian Cancer The methods of the present invention have other applications as well. For example, the biomarkers can be used to screen for compounds that modulate the expression of the biomarkers in vitro or in vivo, which compounds in turn may be useful in treating or preventing ovarian cancer in patients. In another example, the biomarkers can be used to monitor the response to treatments for ovarian cancer. In yet another example, the biomarkers can be used in heredity studies to determine if the subject is at risk for developing ovarian cancer.

Thus, for example, the kits of this invention could include a solid substrate having a hydrophobic function, such as a protein biochip (e.g., a Ciphergen H50 ProteinChip array, e.g., ProteinChip array) and a sodium acetate buffer for washing the substrate, as well as instructions providing a protocol to measure the biomarkers of this invention on the chip and to use these measurements to diagnose ovarian cancer.

Compounds suitable for therapeutic testing may be screened initially by identifying compounds which interact with one or more biomarkers listed in Table 1. By way of example, screening might include recombinantly expressing a biomarker listed in Table 1, purifying the biomarker, and affixing the biomarker to a substrate. Test compounds would then be contacted with the substrate, typically in aqueous conditions, and interactions between the test compound and the biomarker are measured, for example, by measuring elution rates as a function of salt concentration. Certain proteins may recognize and cleave one or more biomarkers of Table 1, in which case the proteins may be detected by monitoring the digestion of one or more biomarkers in a standard assay, e.g., by gel electrophoresis of the proteins.

In a related embodiment, the ability of a test compound to inhibit the activity of one or more of the biomarkers of Table 1 may be measured. One of skill in the art will recognize that the techniques used to measure the activity of a particular biomarker will vary depending on the function and properties of the biomarker. For example, an enzymatic activity of a biomarker may be assayed provided that an appropriate substrate is available and provided that the concentration of the substrate or the appearance of the reaction product is readily measurable. The ability of potentially therapeutic test compounds to inhibit or enhance the activity of a given biomarker may be determined by measuring the rates of catalysis in the presence or absence of the test compounds. The ability of a test compound to interfere with a non-enzymatic (e.g., structural) function or activity of one of the biomarkers of Table 1 may also be measured. For example, the self-assembly of a multi-protein complex which includes one of the biomarkers of Table 1 may be monitored by spectroscopy in the presence or absence of a test compound. Alternatively, if the biomarker is a non-enzymatic enhancer of transcription, test compounds which interfere with the ability of the biomarker to enhance transcription may be identified by measuring the levels of biomarker-dependent transcription in vivo or in vitro in the presence and absence of the test compound.

Test compounds capable of modulating the activity of any of the biomarkers of Table 1 may be administered to patients who are suffering from or are at risk of developing ovarian cancer or other cancer. For example, the administration of a test compound which increases the activity of a particular biomarker may decrease the risk of ovarian cancer in a patient if the activity of the particular biomarker in vivo prevents the accumulation of proteins for ovarian cancer. Conversely, the administration of a test compound which decreases the activity of a particular biomarker may decrease the risk of ovarian cancer in a patient if the increased activity of the biomarker is responsible, at least in part, for the onset of ovarian cancer.

In an additional aspect, the invention provides a method for identifying compounds useful for the treatment of disorders such as ovarian cancer which are associated with increased levels of modified forms of Protein C inhibitor (e.g., M3902, the C-terminal fragment). For example, in one embodiment, cell extracts or expression libraries may be screened for compounds which catalyze the cleavage of Protein C inhibitor or its precursor to produce the C-terminal fragment. In one embodiment of such a screening assay, cleavage of Protein C inhibitor may be detected by attaching a fluorophore to Protein C inhibitor (or its precursor) which remains quenched when Protein C inhibitor is uncleaved, but which fluoresces when the protein is cleaved. Alternatively, a version of full-length Protein C inhibitor (or its precursor) may be modified so as to render the amide bond between amino acids x and y uncleavable may be used to selectively bind or "trap" the cellular protease which cleaves full-length Protein C inhibitor at that site in vivo. Methods for screening and identifying proteases and their targets are well-documented in the scientific literature, e.g., in Lopez-Ottin et al. (*Nature Reviews*, 3:509-519 (2002)).

In yet another embodiment, the invention provides a method for treating or reducing the progression or likelihood of a disease, e.g., ovarian cancer, which is associated with the increased levels of the C-terminal fragment of Protein C inhibitor. For example, after one or more proteins have been identified which cleave Protein C inhibitor, combinatorial libraries may be screened for compounds which inhibit the cleavage activity of the identified proteins. Methods of screening chemical libraries for such compounds are well-known in art. See, e.g., Lopez-Otin et al. (2002). Alternatively, inhibitory compounds may be intelligently designed based on the structure of Protein C inhibitor.

At the clinical level, screening a test compound includes obtaining samples from test subjects before and after the subjects have been exposed to a test compound. The levels in the samples of one or more of the biomarkers listed in Table 1 may be measured and analyzed to determine whether the levels of the biomarkers change after exposure to a test compound. The samples may be analyzed by mass spectrometry, as described herein, or the samples may be analyzed by any appropriate means known to one of skill in the art. For example, the levels of one or more of the biomarkers listed in Table 1 may be measured directly by Western blot using radio- or fluorescently-labeled antibodies which specifically bind to the biomarkers. Alternatively, changes in the levels of mRNA encoding the one or more biomarkers may be measured and correlated with the administration of a given test compound to a subject. In a further embodiment, the changes in the level of expression of one or more of the biomarkers may be measured using in vitro methods and materials. For example, human tissue cultured cells which express, or are capable of expressing, one or more of the biomarkers of Table 1 may be contacted with test compounds. Subjects who have been treated with test compounds will be routinely examined for any physiological effects which may result from the treatment. In particular, the test compounds will be evaluated for their ability to decrease disease likelihood in a subject. Alternatively, if the test compounds are administered to subjects who have previously been diagnosed with ovarian cancer, test compounds will be screened for their ability to slow or stop the progression of the disease.

XII. Examples

EXAMPLE 1

Biomarkers for Detecting Ovarian Cancer

Samples: Ovarian cyst fluid samples were acquired from Sahlgrenska Academy at Goteborg University (Sweden). The samples (187 total) had been collected from patients intra-operatively and stored at −80° C. The samples used for the Standard Profiling Method and High Throughput Sample Fractionation methods described below included 129 benign and 58 ovarian cancer samples (30 stage I/II). For the Immunoprecipitation Method, 40 samples (20 cancer and 20 benign) were used.

I. Standard Profiling Method

10 µl cyst fluid or serum was deposited in each well of 96-well microtiter plate. 50 µl 0.5% SDS HEPES was added. The plate was sealed and incubated at 90° C. for 1 hour. After shaking for 5 minutes with platform shaker (Micromix), 20 µl aliquot was added to 200 µl of buffer in a bioprocessor containing either a cation exchange ProteinChip array (CM10, Ciphergen) or an immunobilized Cu ProteinChip array (IMAC30, Ciphergen). After incubation with shaking for 45 minutes, the arrays were washed once with 200 µl of the same buffer, then rinsed with water. After adding CHCA (alpha-cyano-4-hydroxycinnamic acid), the chip bound proteins were profiled with PCS4000 mass spectrometer (Ciphergen).

II. High Throughput Sample Fractionation by Tandem Equalizer Bead and Mercapto Ethyl Pyridine (MEP) Bead 200 µl cyst fluid or serum was deposited into each well of 96-deepwell plate. 50 µl of a solution containing 2M guanidine thiocyanate, 9 M urea, 2% CHAPS, 50 mM TrisHCl pH 9 was added to each well. After shaking at 4° C. for 20 minutes, each sample was diluted with 500 µl 50 mM TrisHCl containing protease inhibitor cocktail (Roche). This was added to 70 µl 50% v/v Equalizer resin bead (custom synthesized hexapeptide libraries, American Peptide) in FDTS modified fritted 96-deepwell filter plate (Nunc). The plate was sealed, shaken at 4° C. for 60 min, then centrifuged at 1500 rpm for 2 minutes to collect the nonbound fraction. The entire nonbound fraction was transferred to 200 µl 50% v/v MEP Hypercel bead (Pall) in a FDTS modified fritted 96-deepwell filter plate (Nunc). The plate was sealed, shaken at 4° C. for 20 minutes, then centrifuged at 1500 rpm for 2 minutes to collect the Flow Through fraction.

Each well of the 96-well filter plate was washed with 500 µl 50 mM TrisHCl 0.04% Triton X100 pH 7.5 four times.

Proteins bound to the Equalizer beads were differentially eluted by (1)100 µl of 1M NaCl, 50 mM TrisHCl, 0.04% Triton X100, and pH 7.5 to yield Fraction E1, (2) 100 µl of 50% isopropanol/acetonitrile (2:1), 1% Formic acid, and 2% Trifluoroacetic acid to yield Fraction E2, (3) 100 µl of 8M GuanidineHCl, 1% Triton X100 (90 C) to yield Fraction E3a, (4) 100 µl of 6M urea, 30% ethylene glycol, and 0.1M sodium carbonate to yield Fraction E3b.

Proteins bound to the MEP beads were differentially eluted by (1) 150 µl of 50% isopropanol/acetonitrile (2:1), 0.5% Formic acid 1% Trifluoroacetic acid to yield Fraction M1, (2) 150 µl 8M GuanidineHCl, and 1% Triton X100 (90 C) to yield Fraction M2a, (3) 150 µl 6M urea, 30% ethylene glycol, and 0.1M sodium carbonate to yield Fraction M2b.

20-40 µl aliquot of each eluted fraction was added to 200 µl of buffer in a bioprocessor containing either a cation exchange ProteinChip array (CM10, Ciphergen) or immobilized Cu ProteinChip array (IMAC30, Ciphergen). After incubation with shaking for 45 minutes, the arrays were washed with 200 µl of the same buffer once, then rinsed with water. After adding sinapinic acid, the chip bound proteins were profiled with PCS4000 mass spectrometer (Ciphergen).

III. High Throughput Sample Fractionation by Tandem Antibody Libraries Bead

A direct targeting method using immunoprecipitation was also used to measure biomarkers in ovarian cyst fluid. In this approach, biomarkers in ovarian cyst fluid were targeted by selected monoclonal antibody mixtures. Two antibody mixtures were used (Table 3). Antibody mixture II (Ab mix II) was applied to the Antibody Mixture I (Ab Mix I) flow through solution. More detail is provided in the protocol below.

TABLE 3

Targets of Antibody Mixes and Expected m/z Of Targeted Proteins

| Target (Ab mix I) | Expected m/z |
|---|---|
| IL1 beta | 17375 (also prepro-form) |
| IL8 (CXCL8) | 8376/8920 |
| CCL2 (MCP1) | 8664 |
| CCL3 (MIP1alpha) | 7441/7712 |
| CXCL1 (GROalpha) | 7861 |
| CXCL12 (SDF1) | 7606/8297/8520 |
| Target (Ab mix II) | |
| IL6 | 27 kD (+CHO) |
| IL12 | 75 kd (+CHO) |
| TGFbeta | 13 kD (+CHO + latent) |
| TNFalpha | 17350 |
| VEGF | 27-39 KD (+CHO) |
| GCSF | 19 kD (+CHO) |
| bFGF | 18-24 kD (+CHO) |

400 µl cyst fluid was added to a 300 µl solution of 150 mM TrisHCl, 0.15 M NaCl, and 0.1% Tween 20 containing protease inhibitor cocktail (Roche) with 50 µl 50% v/v immobilized Antibody Mix I agarose beads (anti-human Interleukin 8, anti-human Interleukin 1β, anti-human RANTES, anti-human MCP1, anti-human MIP1α, anti-human GROalpha, anti-human SDF1) in an FDTS modified fritted 96-deepwell filter plate (Nunc). The plate was sealed, shaken at 4° C. for 8 hours, then centrifuged at 1500 rpm for 2 minutes to collect the nonbound fraction. The entire nonbound fraction was transferred to 50 µl 50% v/v immobilized Antibody Mix II agarose bead (anti-human Interleukin 6, anti-human Interleukin 12, anti-human TGFbeta, anti-human TNFalpha, anti-human VEGF, anti-human bFGF, anti-human GCSF, anti-human GMCSF) in an FDTS modified fritted 96-deepwell filter plate (Nunc). The plate was sealed, shaken at 4° C. for 8 hours, then centrifuged at 1500 rpm for 2 minutes to remove the nonbound fraction. Each well of the 96-well filter plate was then washed twice with 500 µl 1M urea, 0.1% CHAPS, and phosphate-buffered saline at pH 7.5.

Proteins bound to the Antibody Mix I and Mix II beads were differentially eluted by (1) 100 µl of 50% isopropanovacetonitrile (2:1) 0.5% Forrmic acid 1% Trifluoroacetic acid to yield Fraction B1, (2) 100 µl of 3M Guanidine thiocyanate, 0.5% Triton X100 (90 C) to yield Fraction B2a, (3) 100 µl 2M thiourea, 4 M urea, 1% CHAPS, and 50 mM TrisHCl pH7.5 to yield Fraction B2b.

A 30 µl aliquot of each eluted fraction was added to 200 µl of buffer in a bioprocessor containing either a cation exchange ProteinChip array (CM10, Ciphergen) or an immobilized Cu ProteinChip array (IMAC30, Ciphergen). After incubation with shaking for 45 minutes, the arrays were washed with 200 µl of the same buffer once, then rinsed with water. After adding sinapinic acid, the chip bound proteins were profiled with a PCS4000 mass spectrometer (Ciphergen).

Data Analysis:

Data were acquired using CiphergenExpress. Mass calibration was performed using external calibrants, intensity normalization was based on total ion current using an external normalization factor, and baseline subtraction was performed. Peak detection was performed in CiphergenExpress using the criteria that a peak must have a signal/noise ratio of 3:1 and be present in 20% of the spectra. Statistical analysis was performed in CiphergenExpress using the Mann-Whitney test (for two groups, e.g., benign versus ovarian cancer) or Kruskal-Wallis test (for multiple group comparison, e.g., benign ovarian disease versus ovarian cancer versus ovarian cancer with low malignant potential (LMP) versus other malignancies (such as malignancies other than invasive epithelial ovarian cancer, including metastatic cancer (e.g., gastric cancer frequently metastasizes to the ovary), mesothelioma, a stromal ovarian cancer, etc).

Figure 2:
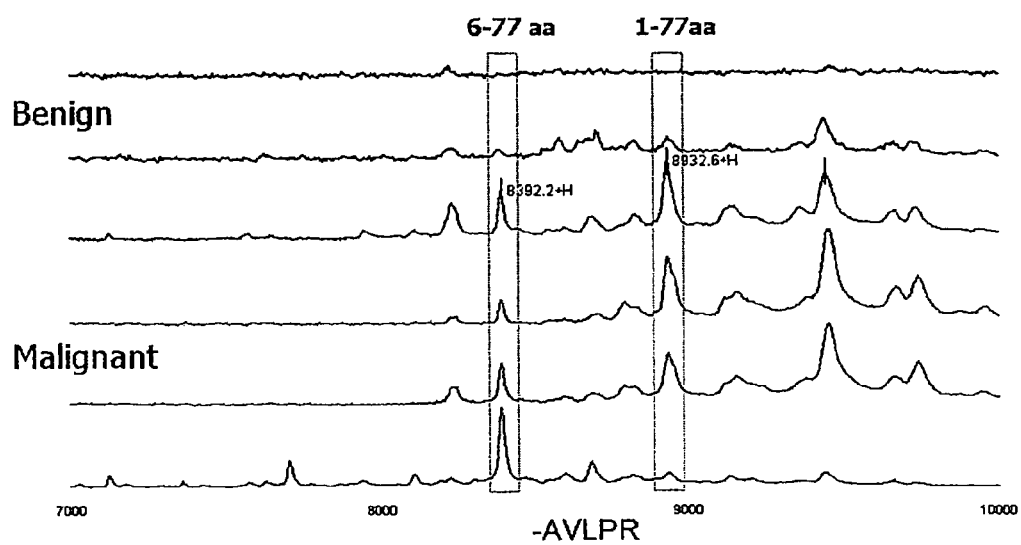
FIG. 2 shows various mass spectrophotometry spectra for IL8 protein and a truncated fragment of IL8 missing five amino acids ('AVLPR' disclosed as SEQ ID NO: 9) from the N-terminus. The protein was isolated from ovarian cyst fluid using the Immunoprecipitation Method (IP-MS). The lower four spectra are from samples taken from patients with malignant ovarian cancer.

Results from the Immunoprecipitation Method of evaluating ovarian cyst proteins are shown in FIG. 1 and FIG. 2.

EXAMPLE 2

Marker Purification and ID

Biomarkers identified using the Profiling Method described above were purified using combinations of chromatographic techniques employing a range of Biosepra sorbents typically followed by SDS-PAGE. The purification schemes were monitored using a ProteinChip Reader to track biomarkers of interest. For proteins smaller than 30 kDa, intact bands of interest were extracted from gels and reanalyzed using the ProteinChip Reader to confirm their exact masses matched with the original biomarker. The gel-extracted proteins were in-solution digested with trypsin, and proteins larger than 30 kDa were in-gel digested. Tryptic digests were analyzed by peptide mapping using the ProteinChip Reader and by tandem MS using a Q-STAR (Applied Biosystems) instrument fitted with a PCI-1000 ProteinChip Interface. Biomarkers smaller than 4 kDa were enriched by combinations of chromatographic techniques and identified directly by tandem MS without SDS-PAGE purification and/or trypsin digestion. In some instances, the biomarkers were identified using antibodies. The techniques thus described were used to identify the biomarkers of Table 1.

Two proteins identified using the Immunoprecipitation Method of analyzing ovarian cyst fluid were MCP-1 and IL-8 (see FIGS. 1 and 2). MCP-1 is monocyte chemotactic protein 1 (SwissProt #P13500) and has the following sequence:

```
        10         20         30         40
QPDAINAPVT CCYNFTNRKI SVQRLASYRR ITSSKCPKEA 50         60         70
VIFKTIVAKE ICADPKQKWV QDSMDHLDKQ TQTPKT
(SEQ ID NO: 6)
```

The N-terminal Q is pyrrolidone carboxylic acid and the protein has a calculated MW of 8664.03 Da.

IL-8 is interleukin 8 (SwissProt #P10145). As shown in FIG. 2, IL-8 is present in ovarian cyst fluid in two forms: a full-length protein and a truncated protein. The full-length protein has the following sequence:

```
        10         20         30         40
AVLPRSAKEL RCQCIKTYSK PFHPKFIKEL RVIESGPHCA 50         60         70
NTEIIVKLSD GRELCLDPKE NWVQRVVEKF LKRAENS
(SEQ ID NO: 7)
``` and a calculated molecular weight of 8918.45 Da. The truncated form (referred to as IL-8 (6-77)), is missing 5 amino acids from the N-terminus and has the following sequence:

```
        10         20         30         40
SAKELRCQCI KTYSKPFHPK FIKELRVIES GPHCANTEII 50         60         70
VKLSDGRELC LDPKENWVQR VVEKFLKRAE NS
(SEQ ID NO: 8)
```

The calculated molecular weight of IL-8 (6-77) is 8381.77 Da.

Ovarian cyst fluid is a prolific source of diagnostic protein biomarkers for ovarian cancer. Some of these biomarker proteins are acute-phase reactants. As demonstrated herein, cyst fluid proteins are an excellent source of biomarkers for use in diagnostic tests for ovarian cancer.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for qualifying ovarian cancer status in a subject comprising:
   (a) measuring at least one biomarker in ovarian cyst fluid, serum, plasma, blood, or urine from the subject, wherein the at least one biomarker is Protein C inhibitor;
   (b) comparing the measurement with a diagnostic amount that distinguishes a positive ovarian cancer status from a negative ovarian cancer status; and
   (c) correlating the comparison with ovarian cancer status, wherein the ovarian cancer status is the presence or absence of ovarian cancer.

2. A method for diagnosing ovarian cancer in a subject, the method comprising:
   (a) measuring at least one biomarker in ovarian cyst fluid, serum, plasma, blood, or urine from the subject, wherein the biomarker is Protein C inhibitor;
   (b) comparing the measurement with a diagnostic amount that distinguishes a positive ovarian cancer status from a negative ovarian cancer status; and
   (c) correlating the comparison with the presence or absence of ovarian cancer.

* * * * *